US012569598B2

(12) United States Patent
Guan et al.

(10) Patent No.: US 12,569,598 B2
(45) Date of Patent: Mar. 10, 2026

(54) METHOD FOR PREPARING POLY (THIOCTIC ACID)-COPPER COATING ON SURFACE OF CARDIOVASCULAR STENT MATERIAL

(71) Applicant: Zhengzhou University, Zhengzhou (CN)

(72) Inventors: Shaokang Guan, Zhengzhou (CN); Zhaoqi Zhang, Zhengzhou (CN); Jingan Li, Zhengzhou (CN); Shijie Zhu, Zhengzhou (CN); Liguo Wang, Zhengzhou (CN); Peiduo Tong, Zhengzhou (CN); Yahui Wang, Zhengzhou (CN)

(73) Assignee: ZHENGZHOU UNIVERSITY, Zhengzhou (CN)

( * ) Notice: Subject to any disclaimer, the term of this patent is extended or adjusted under 35 U.S.C. 154(b) by 288 days.

(21) Appl. No.: 18/515,201

(22) Filed: Nov. 20, 2023

(65) Prior Publication Data

US 2024/0173462 A1     May 30, 2024

Related U.S. Application Data

(63) Continuation-in-part of application No. PCT/CN2023/071523, filed on Jan. 10, 2023.

(51) Int. Cl.
*A61L 31/08*          (2006.01)

(52) U.S. Cl.
CPC ......... *A61L 31/088* (2013.01); *A61L 2420/02* (2013.01); *A61L 2420/06* (2013.01)

(58) Field of Classification Search
None
See application file for complete search history.

(56) References Cited

U.S. PATENT DOCUMENTS 6,288,106 B1 *   9/2001   Pearson ............... C07D 307/62
549/39

OTHER PUBLICATIONS

Zhang et al. (Chemical Engineering Journal 451 (2023)139096).*
Zhang et al. (Chemical Engineering Journal 451 (2023)139096; published online Sep. 8, 2022).*

* cited by examiner

*Primary Examiner* — Anna R Falkowitz
*Assistant Examiner* — Garen Gotfredson
(74) *Attorney, Agent, or Firm* — MATTHIAS SCHOLL P.C.; Matthias Scholl

(57)          ABSTRACT

A method for preparing a poly(thioctic acid)-copper coating (poly(TA-Cu)) on a surface of a cardiovascular stent material includes: grinding a cardiovascular stent material with sandpaper until the surface of the cardiovascular stent material is flat and smooth, rinsing the cardiovascular stent material with deionized water and anhydrous ethanol in sequence, and drying the cardiovascular stent material to obtain a pre-treated cardiovascular stent material; dissolving thioctic acid in an alcoholic solvent, adding anhydrous copper chloride to a mixed solution of thioctic acid and the alcoholic solvent, stirring the mixed solution, to yield a precursor solution; treating the pre-treated cardiovascular stent material with the precursor solution, and drying, thus forming a poly(thioctic acid)-copper coating on the surface of the pre-treated cardiovascular stent material. The concentration of thioctic acid in the alcoholic solvent is 0.1-0.3 g/mL, and the molar ratio of anhydrous copper chloride to thioctic acid monomer is 1:100-5000.

5 Claims, 11 Drawing Sheets

EHT = 2.00 kV        Signal A = SE2
WD = 7.4 mm          Mag = 1.00 K X

10 μm

After coating

Before coating

1

METHOD FOR PREPARING POLY (THIOCTIC ACID)-COPPER COATING ON SURFACE OF CARDIOVASCULAR STENT MATERIAL

CROSS-REFERENCE TO RELATED APPLICATIONS

This application is a continuation-in-part of International Patent Application No. PCT/CN2023/071523 with an international filing date of Jan. 10, 2023, designating the United States, now pending, and further claims foreign priority benefits to Chinese Patent Application No. 202211508122.2 filed Nov. 29, 2022. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

BACKGROUND

The disclosure relates to the field of cardiovascular stents, and more particularly to a method for preparing a poly (thioctic acid)-copper coating (poly(TA-Cu)) on a surface of a cardiovascular stent material.

Conventional coatings of drug eluting stents (DES) are mainly polyesters loaded with drugs such as rapamycin and its derivatives or paclitaxel. The polyester is polylactic acid, polylactic acid-hydroxyacetic acid, or polycaprolactone. However, these polymers and their degradation products have no therapeutic effects and sometimes bring additional side effects. The drug eluting coating also inhibits the growth of endothelial cells, leading to delayed endothelialization. In addition, the coating of the drug eluting stents is costly, which increases the economic burden on patients.

SUMMARY

To address the issue of delayed endothelialization in existing drug-eluting stents. The disclosure provides a simple and cost-effective method for preparing a poly(TA-Cu) coating on a surface of a cardiovascular stent material. The method yields a uniformly dense poly(TA-Cu) coating with robust adhesion properties. The cardiovascular stent, when coated with the poly(TA-Cu), enhances endothelial cell proliferation, accelerates endothelialization, and provides anti-thrombotic effects, thereby decreasing the occurrence of late stent thrombosis.

The method for preparing a poly(TA-Cu) coating on the surface of cardiovascular stent material, and the method comprises:

(1) grinding, by using sandpaper, a cardiovascular stent material to an even an and polished surface; rinsing the cardiovascular stent material with deionized water and anhydrous ethanol in sequence to obtain a pre-treated cardiovascular stent; and (2) dissolving thioctic acid in an alcohol solvent to form a mixture, adding anhydrous copper chloride to the mixture to form a mixed solution; stirring the mixed solution, to yield a precursor solution; treating the pre-treated cardiovascular stent material with the precursor solution, and drying, thus forming a poly(TA-Cu) coating on the surface of the pre-treated cardiovascular stent material.

In a class of this embodiment cardiovascular stent material comprises magnesium alloy, zinc alloy, iron alloy, 316L stainless steel, polylactic acid, nickel-titanium alloy, or cobalt-chromium alloy.

In a class of this embodiment, the alcohol solvent comprises anhydrous methanol or anhydrous ethanol.

In a class of this embodiment, a concentration of thioctic acid in the alcohol solution is 0.1 g/mL to 0.3 g/mL, and a molar ratio of anhydrous copper chloride to thioctic acid monomers is between 1:100 and 1:5000.

In a class of this embodiment, the pre-treated cardiovascular stent material is treated with the precursor solution through dip-coating, spin-coating, or spray-coating, to form the poly(TA-Cu) coating on the surface of the pre-treated cardiovascular stent material.

In a class of this embodiment, the method further comprises disposing a magnesium fluoride conversion layer on the surface of the pre-treated cardiovascular stent material; specifically, submerging a magnesium alloy into a hydrofluoric acid solution; allowing the magnesium alloy and the hydrofluoric acid solution to react at room temperature for 40-50 hours; cleaning and drying a resulting product, to achieve a magnesium fluoride conversion layer on the surface of the pre-treated cardiovascular stent material. The hydrofluoric acid solution has a concentration of 35-40 wt. %. The magnesium fluoride conversion layer is then treated with the precursor solution, to form the poly(TA-Cu) coating on the magnesium fluoride conversion layer.

In a class of this embodiment, the poly(TA-Cu) coating has a thickness of 4-6 μm; and the magnesium fluoride conversion layer has a thickness of 1.5-3 μm.

The disclosed method offers advantages, including cost-effectiveness, ease of operation, and the ability to produce a dense and uniform poly(TA-Cu) coating on the surface of the cardiovascular stent material, characterized by strong adhesion. The poly(TA-Cu) coating inhibits platelet adhesion and activation while promoting endothelial cell proliferation.

In the poly(TA-Cu) coating, poly(TA-Cu) polymers form a chelation bond with copper ions ($Cu^{2+}$) to promote the generation of nitric oxide (NO) within the human body. The enhancement occurs because $Cu^{2+}$ acts as catalyst for the conversion of endogenous nitrosothiol donors into NO. NO is a crucial bioactive molecule released by endothelial cells, playing a vital role in the normal function of blood vessels. NO plays a series of biological roles, such as preventing platelet adhesion/aggregation, inhibiting the proliferation of smooth muscle cells, reducing inflammatory, scavenging free radicals, preventing atherosclerosis, and facilitating endothelial repair after injury. As a result, the application of the poly(TA-Cu) coating to the surface of the cardiovascular stent material serves to achieve anticoagulation after implantation, expedite in-situ endothelialization, and ultimately mitigate the risk of acute thrombosis, excessive smooth muscle proliferation, and late adverse events.

DETAILED DESCRIPTION

Figure 1:
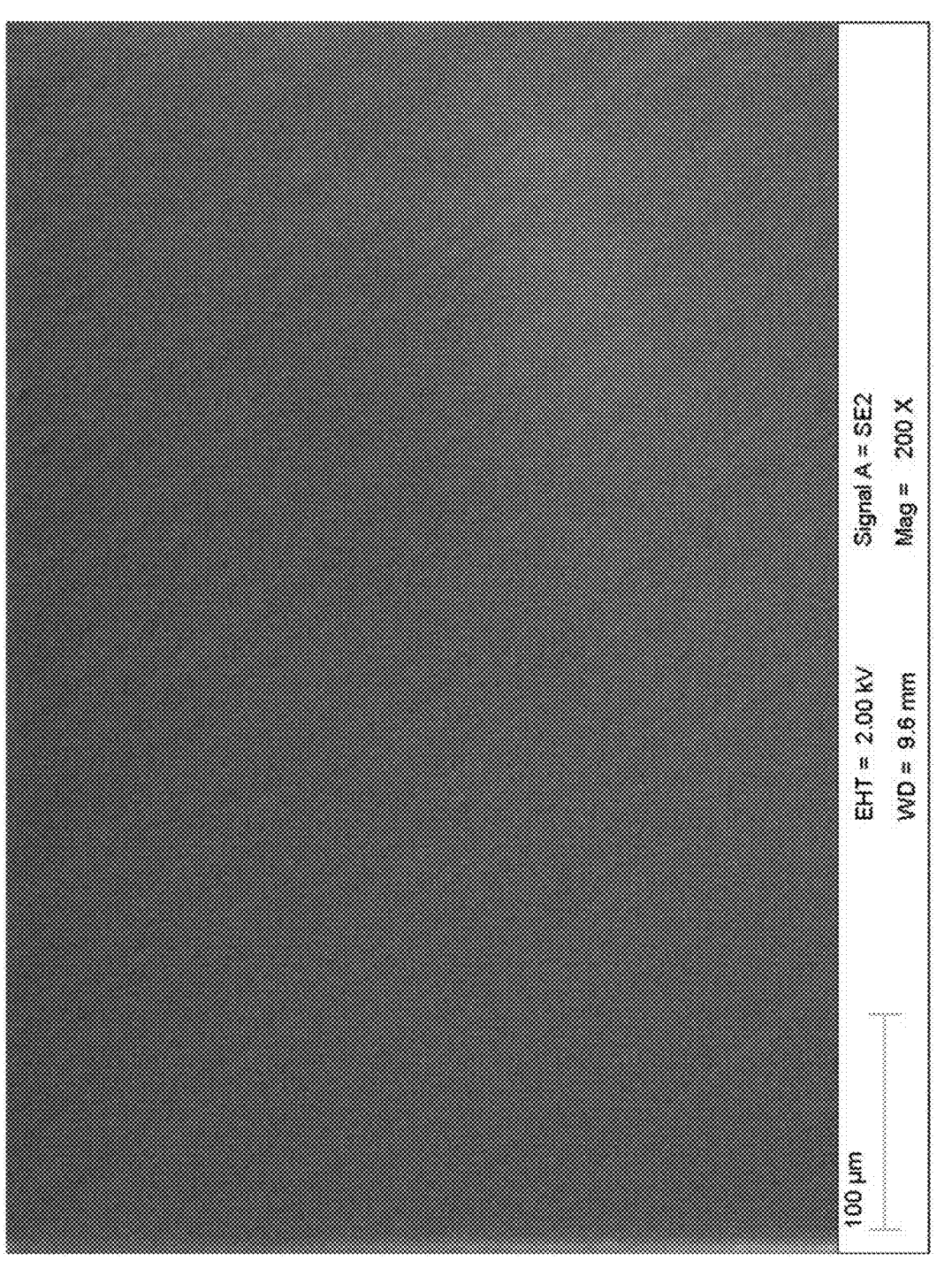
FIG. 1 is a scanning electron microscope (SEM) image of a magnesium fluoride-poly(TA-Cu) coating prepared according to Example 1 of the disclosure.

To further illustrate the disclosure, embodiments detailing a method for preparing a poly(thioctic acid)-copper coating (poly(TA-Cu)) on a surface of a cardiovascular stent material are described below. It should be noted that the following embodiments are intended to describe and not to limit the disclosure.

The cardiovascular stent materials used in the disclosure are sourced from Zhengzhou University's Material Research Center or commercial suppliers.

Example 1

A method for preparing a poly(TA-Cu) coating on a surface of a cardiovascular stent material comprising magnesium alloy is described as follows:

The cardiovascular stent material comprises magnesium alloy known as Mg-2.0Zn-0.5Y-0.5Nd (grade ZE21B), and a method for preparing the cardiovascular stent material is detailed in Chinese patent application No. CN201110043303.8). The method comprises:

Step 1: Pretreatment of a Magnesium Alloy Material a section of magnesium alloy material of the cardiovascular stent material was cut into a cylindrical shape measuring 10 mm in diameter and 3 mm in a thickness, polished to achieve a smooth and oxide-free surface, rinsed with deionized water and anhydrous ethanol in sequence, and dried for subsequent use;

Step 2: Preparation of a Magnesium Fluoride Conversion Layer in a 24-well plate (with a diameter of 1.5 cm and a depth of 2 cm, capable of holding 3.3 mL of solution), 2 mL of 40 wt. % hydrofluoric acid solution was added;

the pretreated magnesium alloy material was placed within the 24-well plate containing the 40 wt. % hydrofluoric acid solution;

the 24-well plate was then placed in a fume hood at room temperature for 48 hours, so that a magnesium fluoride conversion layer is formed on the magnesium alloy material; the coated magnesium alloy material was rinsed with deionized water and anhydrous ethanol in sequence, to remove residual hydrofluoric acid, and then dried;

Step 3: Preparation of a Poly(TA-Cu) Coating thioctic acid was dissolved in anhydrous ethanol to achieve a concentration of 0.15 g/mL; anhydrous copper chloride was added, with a molar ratio of anhydrous copper chloride to thioctic acid of 1:1000;

the coated magnesium alloy material was submerged in a 100 ml beaker containing 53 mL of a mixed solution of thioctic acid and copper chloride, and allowed to stand for 5 seconds; then the beaker was transferred into an oven and dried at 40° C. for 30 minutes, thereby forming a poly(TA-Cu) coating on the magnesium fluoride conversion layer; in other words, a magnesium fluoride-poly(TA-Cu) coating was formed on the surface of the cardiovascular stent material.

The cardiovascular stent material, coated with the magnesium fluoride-poly(TA-Cu) coating, were placed inside a sample bag and sealed.

The magnesium fluoride-poly(TA-Cu) coating, as prepared in Example 1, underwent a series of tests and analysis, comprising scanning electron microscopy (SEM), energy-dispersive X-ray spectroscopy (EDS), Raman spectroscopy, Fourier-transform infrared spectroscopy (FT-IR), micro-nano scratch testing, potentiodynamic polarization curve analysis, catalytic NO generation experiment, platelet adhesion testing, and endothelial cell proliferation testing. The results are shown in FIGS. 1 to 9.

FIG. 1 is an SEM image of the magnesium fluoride-poly(TA-Cu) coating prepared in Example 1. As depicted in FIG. 1, the magnesium fluoride-poly(TA-Cu) coating exhibit a uniform and compact surface structure.

Figure 2:
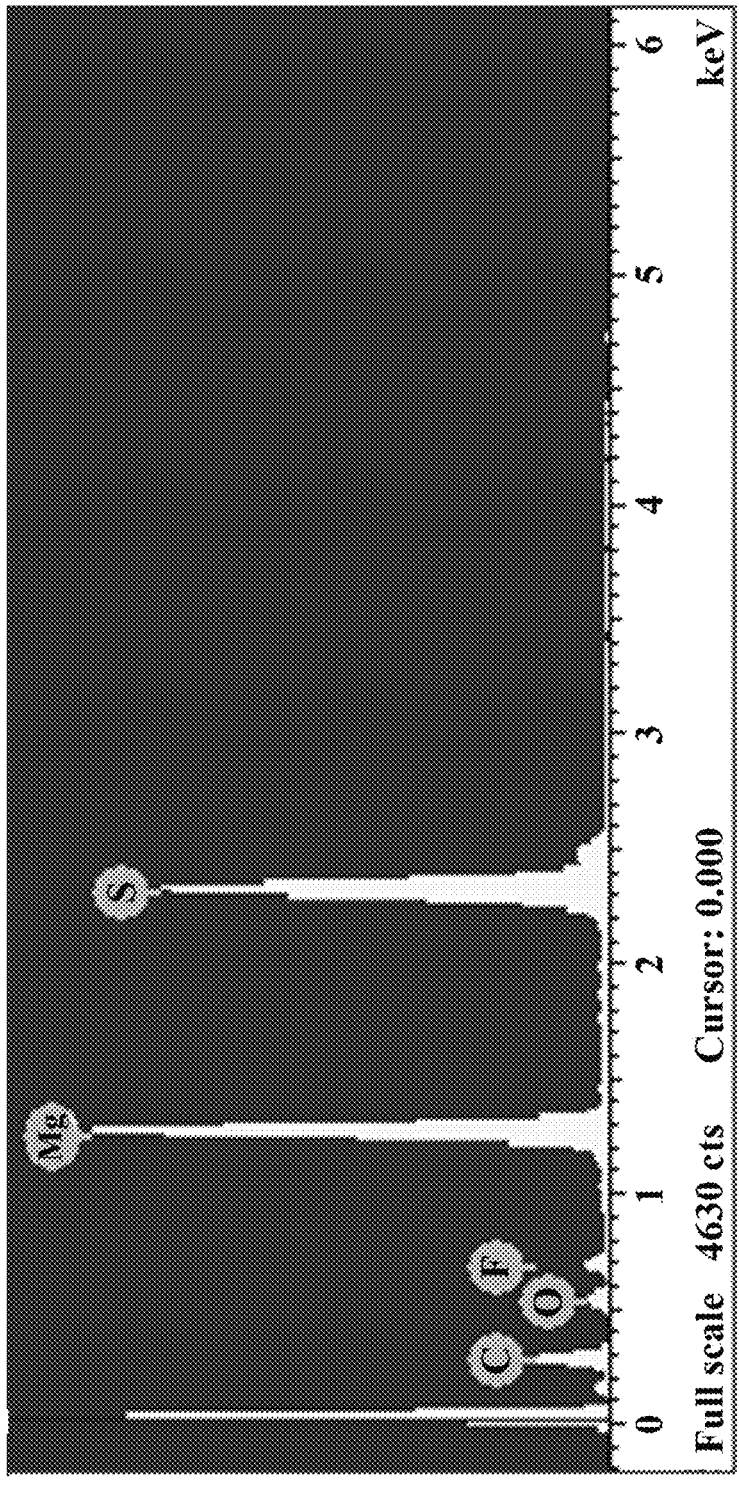
FIG. 2 is an energy-dispersive X-ray spectroscopy (EDS) image of a magnesium fluoride-poly(TA-Cu) coating prepared according to Example 1 of the disclosure.

FIG. 2 is an EDS image of the magnesium fluoride-poly(TA-Cu) coating prepared in Example 1. As depicted in FIG. 2, the magnesium fluoride-poly(TA-Cu) coating contains a moderate level of magnesium (Mg) element and a limited amount of fluorine (F) element, indicating the successful formation of the magnesium fluoride conversion layer on the surface of the magnesium alloy material. Moreover, the surface of the magnesium fluoride-poly(TA-Cu) coating exhibits the highest concentration of sulfur (S) element, accompanied by the presence of carbon (C) and oxygen (O) elements, confirming the successful preparation of the magnesium fluoride-poly(TA-Cu) coating on the magnesium alloy material. The absence of detectable copper (Cu) element may be due to their low concentration.

Figure 3:
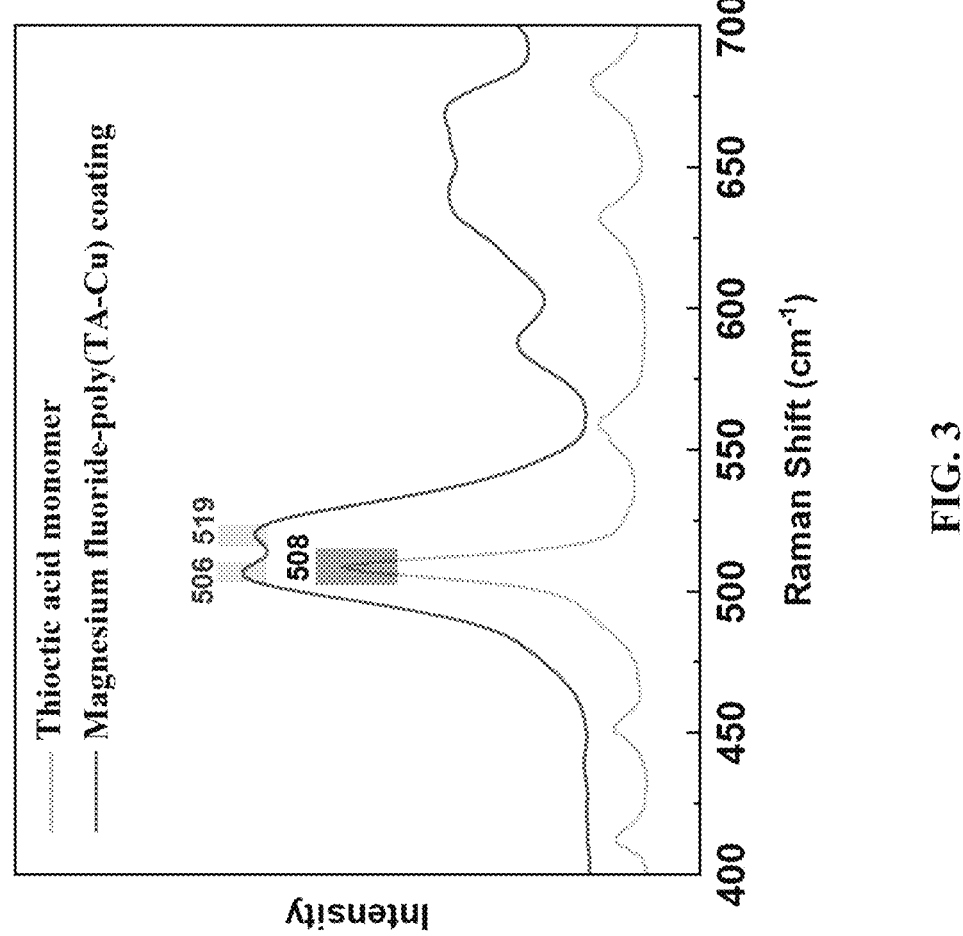
FIG. 3 is a Raman spectrum of a magnesium fluoride-poly(TA-Cu) coating prepared according to Example 1 of the disclosure.

FIG. 3 is a Raman spectrum of the magnesium fluoride-poly(TA-Cu) coating prepared in Example 1. As depicted in FIG. 3, a distinct peak at 508 cm$^{-1}$, associated with thioctic acid monomers, is discernible, corresponding to the disulfide bond. Notably, within the poly(TA-Cu) coating, a characteristic peak of the disulfide bond is splits into two separate peaks at 506 cm$^{-1}$ and 519 cm$^{-1}$. The observed phenomenon verified the occurrence of ring-opening polymerization of thioctic acid into poly(TA-Cu).

Figure 4:
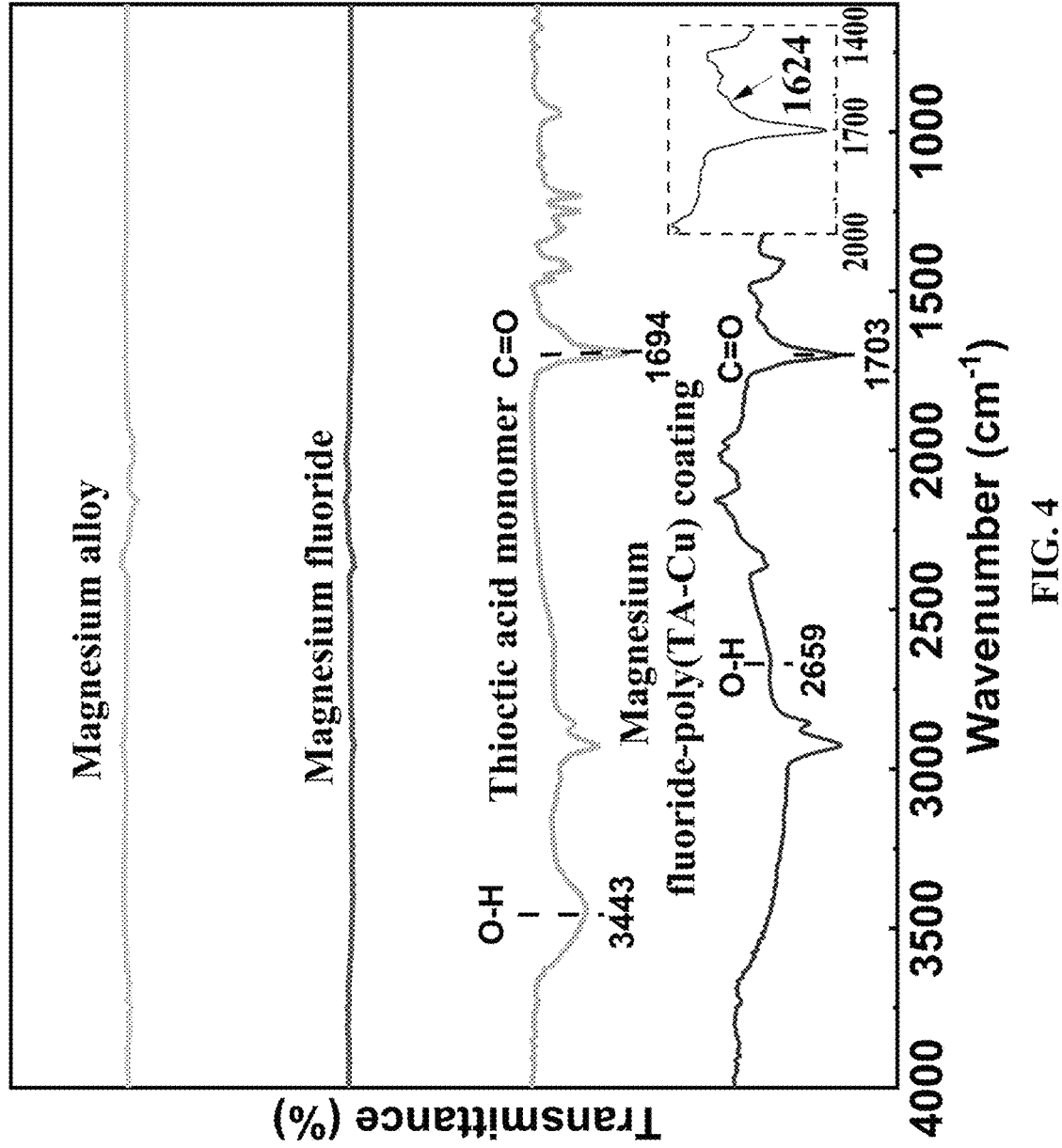
FIG. 4 is a Fourier-transform infrared (FT-IR) spectrum of a magnesium fluoride-poly(TA-Cu) coating prepared according to Example 1 of the disclosure.

FIG. 4 is an FT-IR spectrum of the magnesium fluoride-poly(TA-Cu)) coating prepared in Example 1. As depicted in FIG. 4, in the spectrum of the thioctic acid monomers, a prominent absorption peak at 1694 cm$^{-1}$ signifies the presence of a C=O stretching vibration peak, likely originating from the carboxylic acid groups present in the thioctic acid monomers. In contrast to the C=O stretching vibration peak observed in the thioctic acid monomers, the C=O peak in the poly(TA-Cu) coating shifts to a higher wavenumber at 1703 cm$^{-1}$. The shift is attributed to the formation of hydrogen bonds between carboxyl groups with $Cu^{2+}$, resulting in an intensified stretching vibration of C=O bonds within the poly(TA-Cu) coating. Additionally, a new absorption peak emerging at 1624 $cm^{-1}$ in the FT-IR spectrum corresponds to the asymmetric stretching vibration of coordinated carboxyl groups, providing further confirmation of a robust complex formed between $Cu^{2+}$ and carboxylic acid groups.

Figure 5:
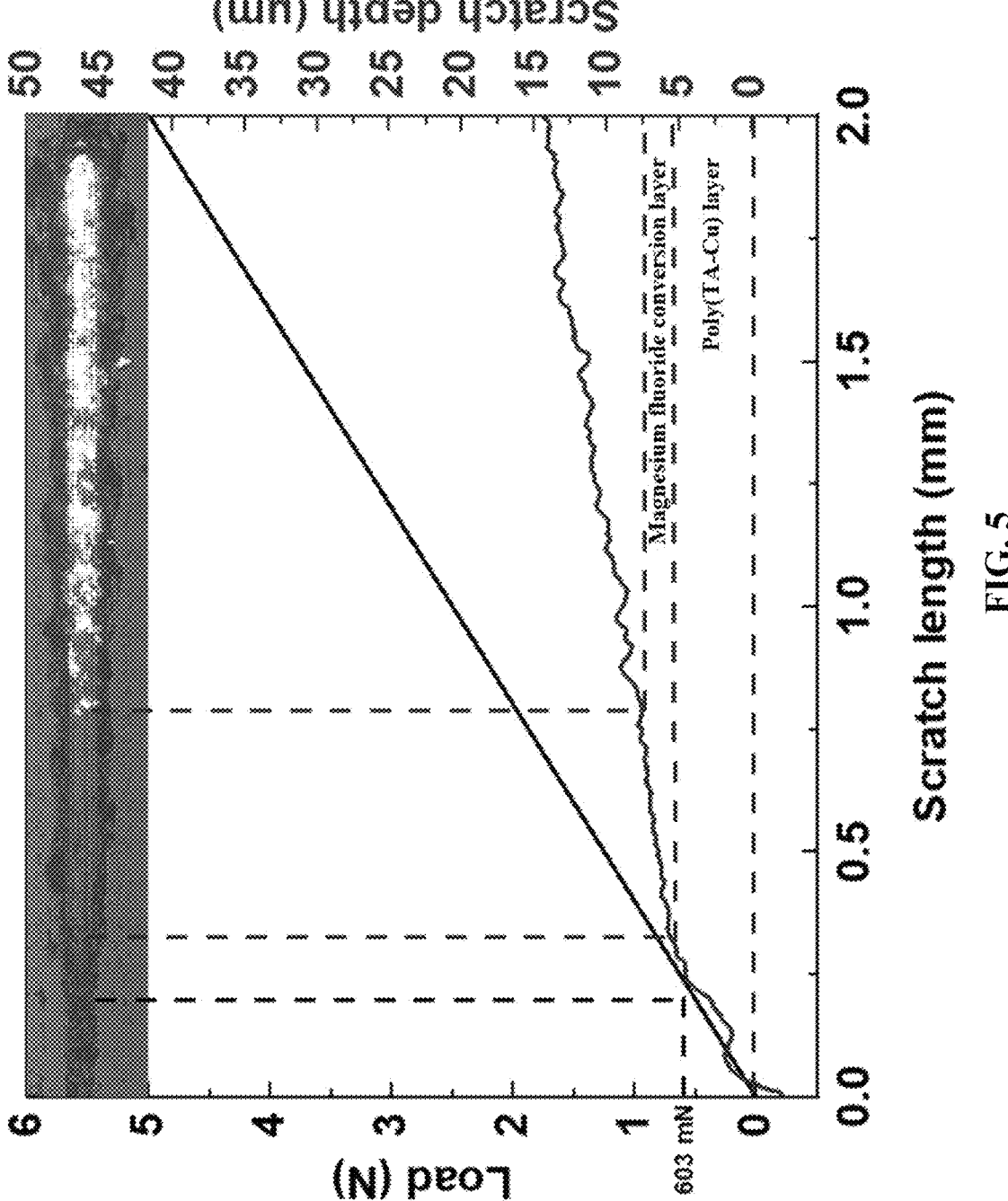
FIG. 5 shows the results of a micro-nano scratch test conducted on a magnesium fluoride-poly(TA-Cu) coating prepared according to Example 1 of the disclosure.

FIG. 5 shows the results of a micro-nano scratch test conducted on the magnesium fluoride-poly(TA-Cu) coating prepared in Example 1. The micro-nano scratch test was carried out as follows: a constant indentation rate of 2 mm/min was maintained while gradually applying a linear load to 5 N (at a loading rate of 5 N/min) until a maximum indentation depth of 2 mm was achieved. As depicted in FIG. 5, the adhesion strength of the magnesium fluoride-poly(TA-Cu) coating is 603.0 mN, confirming a robust bond within the magnesium fluoride-poly(TA-Cu) coating. Moreover, variations in the indentation depth provide insights into the thickness of the magnesium fluoride-poly(TA-Cu) coating. Specifically, the poly(TA-Cu) coating has a thickness of 5.5 μm, and the magnesium fluoride conversion layer has a thicknesses of 2.0 μm.

Figure 6:
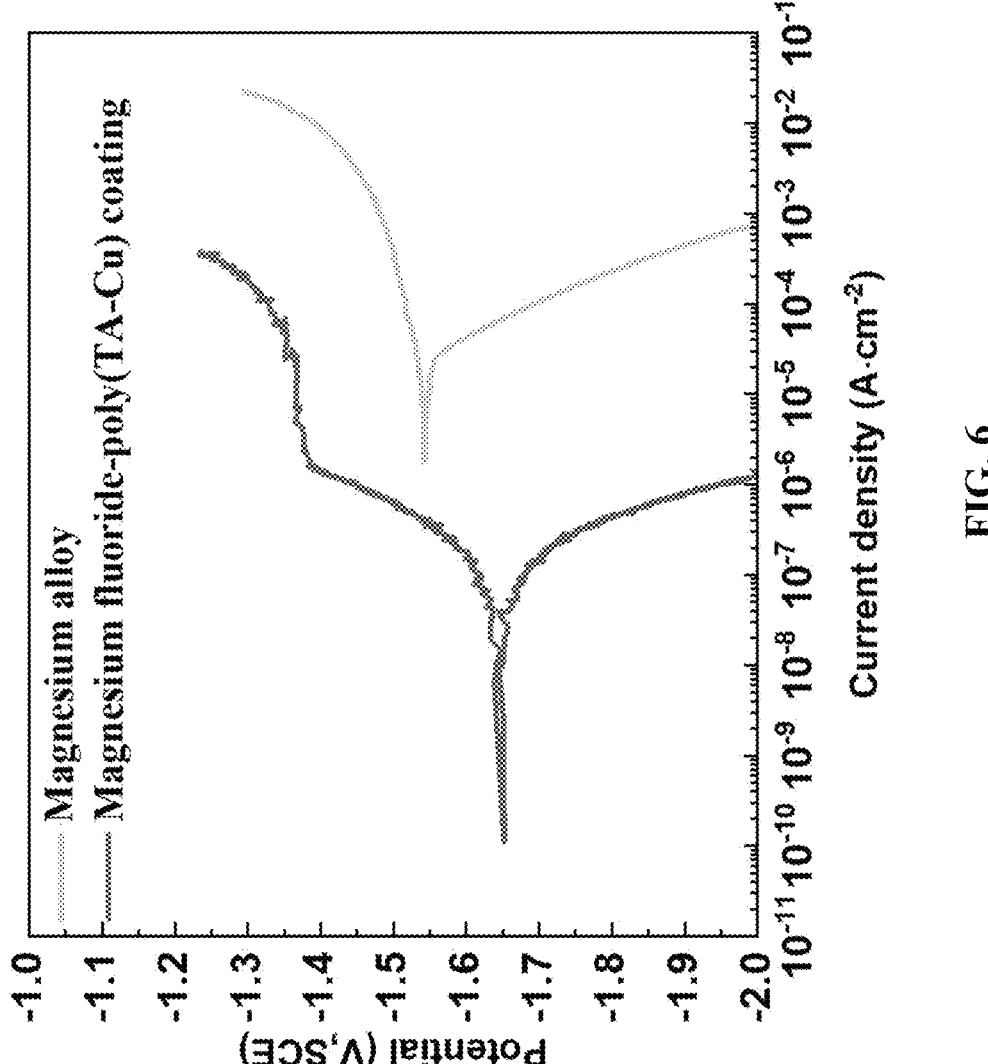
FIG. 6 is a potentiodynamic polarization curve of a magnesium fluoride-poly(TA-Cu) coating prepared according to Example 1 of the disclosure.

FIG. 6 is a dynamic potentiodynamic polarization curve for the magnesium fluoride-poly(TA-Cu) coating prepared in Example 1. A specific testing procedure was carried out as follows: all electrochemical tests were conducted using an electrochemical workstation with a Hank's balanced salt solution as an electrolyte at a temperature of 37° C.; all the electrochemical tests were performed in a conventional three-electrode system; the conventional three-electrode system comprises a platinum sheet functioning as a counter electrode, a saturated calomel electrode functioning as a reference electrode, and a sample with an exposed area of 0.78 $cm^2$ functioning as a working electrode; the sample comprises a magnesium alloy material coated with the magnesium fluoride-poly(TA-Cu), and an uncoated magnesium alloy substrate; before conducting the electrochemical tests, the open-circuit potential of the sample was continuously monitored for 10 minutes until the open-circuit potential reached a stable state; subsequently, the potentiodynamic polarization curve was generated by scanning from −2.0 V to 0.0 V at a constant scan rate of 1.0 $mV \cdot s^{31\ 1}$, and a plurality of electrochemical parameters were derived using the Tafel extrapolation method. As illustrated in FIG. 6, a comparative assessment demonstrates a substantial decrease in self-corrosion current density for the coated magnesium alloy material when contrasted with the uncoated magnesium alloy substrate. The self-corrosion current density declines from $2.90 \times 10^{-5}$ $A/cm^2$ to $9.16 \times 10^{-8}$ $A/cm^2$, marking a reduction of three orders of magnitude. These results signify that the magnesium fluoride-poly(TA-Cu) coating bolsters the corrosion resistance of the uncoated magnesium alloy substrate.

Figure 7:
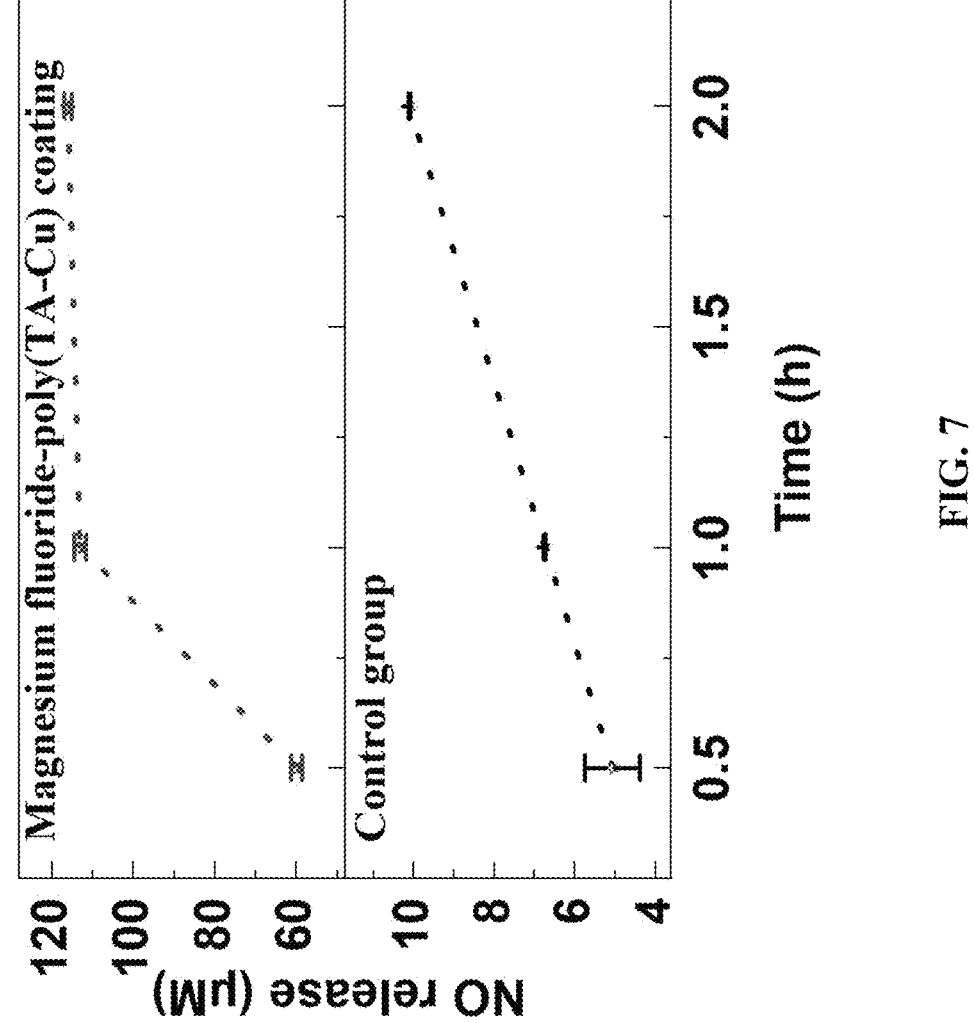
FIG. 7 shows the results of a catalytic NO generation experiment conducted on a magnesium fluoride-poly(TA-Cu) coating prepared according to Example 1 of the disclosure.

FIG. 7 shows the results of a catalytic NO generation experiment conducted on the magnesium fluoride-poly(TA-Cu) coating prepared in Example 1. A specific experimental procedure was carried out as follows: NO generation rate was evaluated using an NO assay kit. Specifically, a magnesium alloy material coated with the magnesium fluoride-poly(TA-Cu) were submerged in 2 mL of PBS (pH 7.4) containing NO donors (comprising 260 mM SNAP and 120 mM GSH). In contrast, a control group was treated with pure PBS lacking NO donors. Following incubation at 37° C. for 0.5, 1.0, and 2.0 hours, the NO assay kit was employed to quantify the concentration of NO generated within the soaking solution. The testing process strictly followed the instructions provided in the assay kit manual. Subsequently, the soaking solution was stained with the Griess reagent, and the absorbance of the soaking solution was measured at 540 nm using a UV spectrophotometer. The principle underlying the NO assay kit is that the magnesium alloy material, coated with the magnesium fluoride-poly(TA-Cu), catalytically induces the release of NO from the NO donors, and the generated NO is easily oxidized into $NO_2^-$. $NO_{2-}$ quickly reacts with the Griess reagent to form a pink-colored azo compound. As depicted in FIG. 7, in the control group, due to the gradual decomposition of NO donors, the release of NO exhibited a slow and linear curve during the test period (0.5 h, 5.050 μM; 1.0 h, 6.735 μM; 2.0 h, 10.105 μM). In contrast, the presence of the magnesium fluoride-poly(TA-Cu) coating resulted in a higher concentration of NO generation (0.5 h, 59.895 μM; 1.0 h, 113.013 μM; 2.0 h, 115.956 μM), signifying that $Cu_2^+$ actively catalyze the decomposition of the NO donors.

Figure 8:
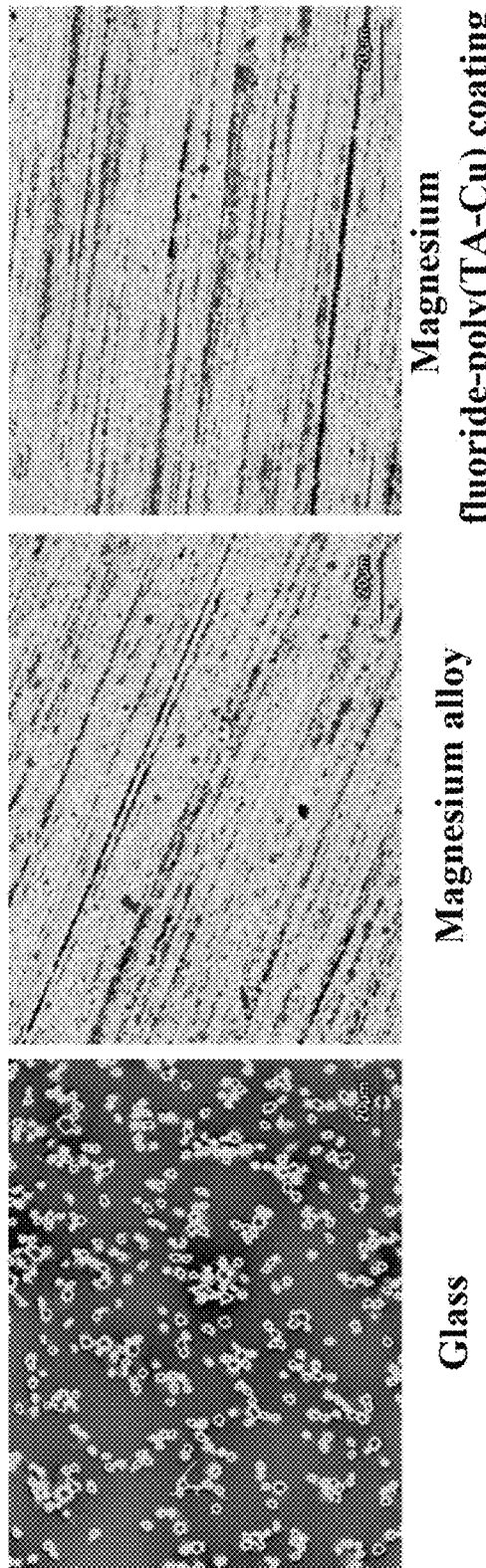
FIG. 8 is a laser confocal image illustrating the results of a platelet adhesion experiment conducted on a magnesium fluoride-poly(TA-Cu) coating prepared according to Example 1 of the disclosure.

FIG. 8 shows laser confocal microscopy images illustrating the results of a platelet adhesion experiment conducted on a clean glass slide, a magnesium alloy material, and the magnesium fluoride-poly(TA-Cu) coating prepared in Example 1. A specific procedure was carried out as follows: 2 mL of peripheral blood was drawn from healthy volunteers; 3.2% sodium citrate was added to the peripheral blood to form anticoagulated whole blood; the anticoagulated whole blood was centrifuged (at 1000 r/min for 10 min) to isolate platelet-rich plasma; a 5 μL of platelet-rich plasma was dropped onto the samples; the samples comprise the clean glass slide, the magnesium alloy material, and the magnesium fluoride-poly(TA-Cu) coating; the samples were then incubated at 37° C. for 60 minutes, with the clean glass slide serving as a control group; any unbound platelet-rich plasma was rinsed with saline; the platelets adhering to the samples were fixed with 4% paraformaldehyde at room temperature for 10 minutes and then rinsed with saline; and the platelet adhesion behavior on the samples was examined using laser scanning confocal microscopy. As illustrated in FIG. 8, a substantial quantity of platelets adhered to the surface of the clean glass slide (the control group), with some platelets extending pseudopods, indicating a typical activated state and verifying the normal functionality of platelet in the experiment. While a few platelets were observed on the surface of the magnesium alloy material, the number of adhered platelets was lower compared to the surface of clean glass slide, and no platelets exhibited signs of activation. No indications of platelet adhesion were observed on the magnesium fluoride-poly(TA-Cu) coating, implying that the magnesium fluoride-poly(TA-Cu) coating significantly inhibit platelet adhesion and aggregation, thereby exerting an anticoagulant effect.

Figure 9:
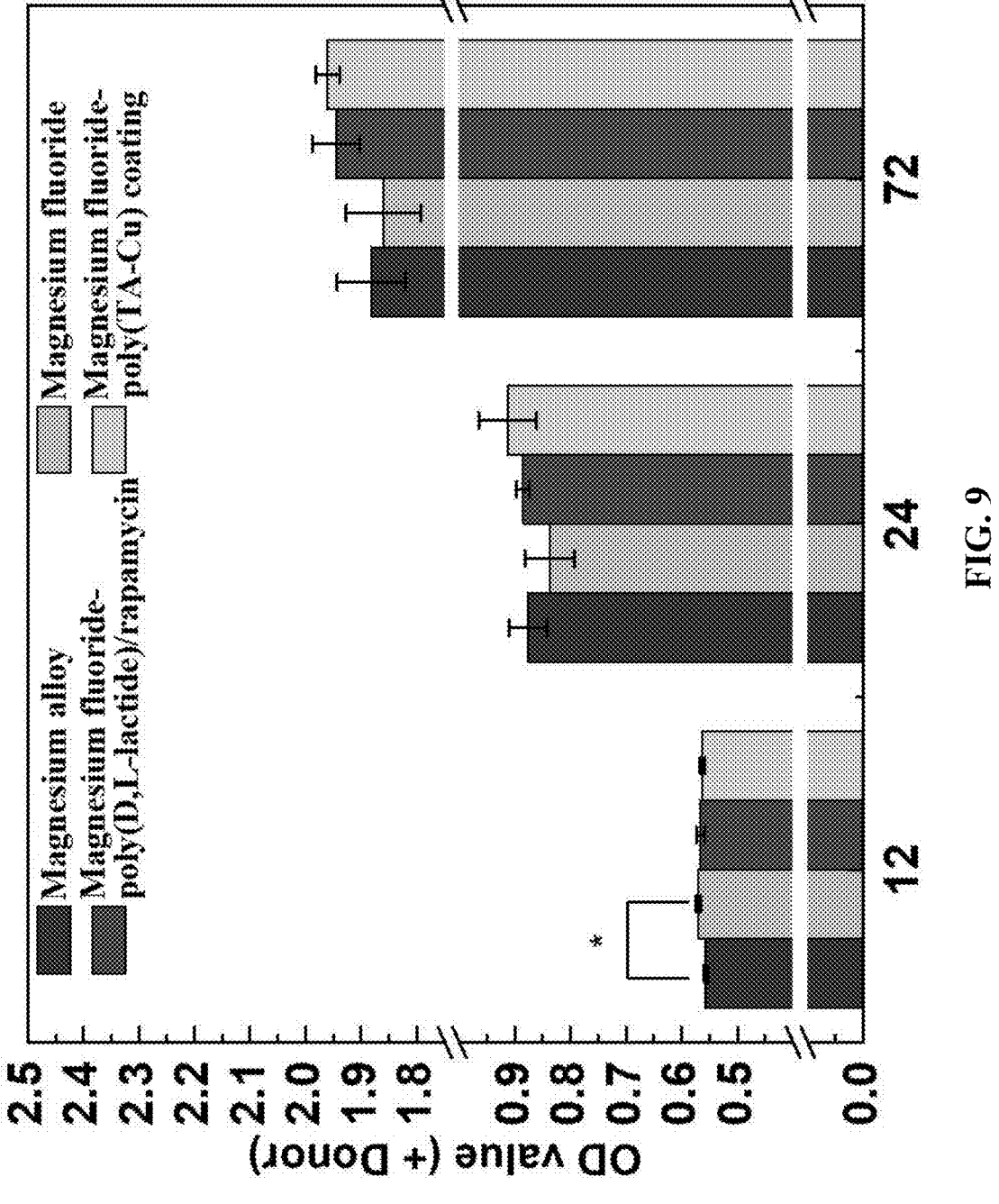
FIG. 9 shows the results of an endothelial cell proliferation experiment conducted on a magnesium fluoride-poly(TA-Cu) coating prepared according to Example 1 of the disclosure.

FIG. 9 shows the results of an endothelial cell proliferation experiment conducted on samples comprising a magnesium alloy material, the magnesium fluoride conversion layer prepared in step 2 of Example 1, a magnesium fluoride-poly(D, L-lactide)/rapamycin/rapamycin) coating (a drug-eluting stent coating), and the magnesium fluoride-poly(TA-Cu) coating prepared in Example 1. A preparation method for the magnesium fluoride-poly(D,L-lactide)/rapamycin coating was referenced from Yuan (Materials Science and Engineering C, 80(2017), 1-6) with slight modifications; specifically, 170 mg of poly(D,L-lactide) (with an average molecular weight of 100,000 g/mol) and 30 mg of rapamycin were dissolved in 20 mL of a dichloromethane solvent with stirring for 5 minutes until complete dissolution, thereby forming the poly(D,L-lactide)/rapamycin coating; subsequently, the poly(D,L-lactide)/rapamycin coating was applied onto the surface of the magnesium fluoride conversion layer using spin-coating technology, followed by removal of dichloromethane through drying; and the poly (D,L-lactide)/rapamycin coating had a thickness of 5.2 μm. The endothelial cell proliferation experiment was carried out as follows: the endothelial-promoting properties of the samples were assessed through an indirect method (using an extract solution); endothelial cells were digested with trypsin to obtain a single-cell suspension; the cells were counted and the cell concentration was adjusted to $4\times10^4$ cells/mL; subsequently, the front and back sides of all the samples were irradiated with ultraviolet light (UV, wavelength 254 nm, sterilization temperature 27° C.) for 60 minutes each; the extract solution was prepared based on the fixed surface area-to-volume ratio (1.25 cm²/mL, according to ISO 10993-5); the endothelial cells ($4\times10^3$ cells/well) were seeded in a 96-well plate and cultured overnight in a humidified incubator (37° C. and 95% relative humidity, with 5% $CO_2$); then, a culture medium containing the extract solution ($V_{extract\ solution}:V_{complete\ medium}=1:1$) was added to each well, and the endothelial cells were cultured for 12, 24, and 72 hours; the culture medium was aspirated, and each well was rinsed with PBS; subsequently, 100 μL of fresh medium containing 10% CCK-8 was added to each well, and the cells were incubated for 2 hours in a cell culture incubator (37° C. and 95% relative humidity, with 5% $CO_2$); and the absorbance of the cells at 450 nm was measured using an enzyme-linked immunosorbent assay (ELISA) reader. As shown in FIG. 9, after 24 and 72 hours of incubation, the magnesium fluoride-poly(TA-Cu) coating exhibited higher optical density (OD) values compared to the magnesium alloy material, the magnesium fluoride conversion layer, and the magnesium fluoride-poly(D, L-lactide)/rapamycin coating; the results indicate that the magnesium fluoride-poly(TA-Cu) coating significantly promotes the proliferation of the endothelial cells.

Example 2

A method for preparing a poly(TA-Cu) coating on a surface of a cardiovascular stent material comprising 316L stainless steel is described as follows:
Step 1. Pretreatment of 316L Stainless Steel
A section of 316L stainless steel material of the cardiovascular stent material was cut into a square piece of 10×10×1 mm, polished to achieve a smooth and even surface, and rinsed with deionized water and anhydrous ethanol in sequence, then dried and sealed for storage.
Step 2 Preparation of a Poly(TA-Cu) Coating
Thioctic acid was dissolved in anhydrous ethanol to reach a concentration of 0.2 g/mL, followed by the addition of anhydrous copper chloride; and a molar ratio of anhydrous copper chloride to thioctic acid is 1:500.
The square piece of 316L stainless steel material was submerged in a 100 mL beaker containing 53 mL of a mixed solution of thioctic acid and copper chloride, allowed to stand for 5 seconds, transferred into an oven, and dried at 40° C. for 30 minutes, thereby forming a poly(TA-Cu) coating on the surface of the cardiovascular stent comprising 316L stainless steel.
The square piece of 316L stainless steel material, coated with the poly(TA-Cu), was placed inside a sample bag and sealed for storage.

8

Figure 10:
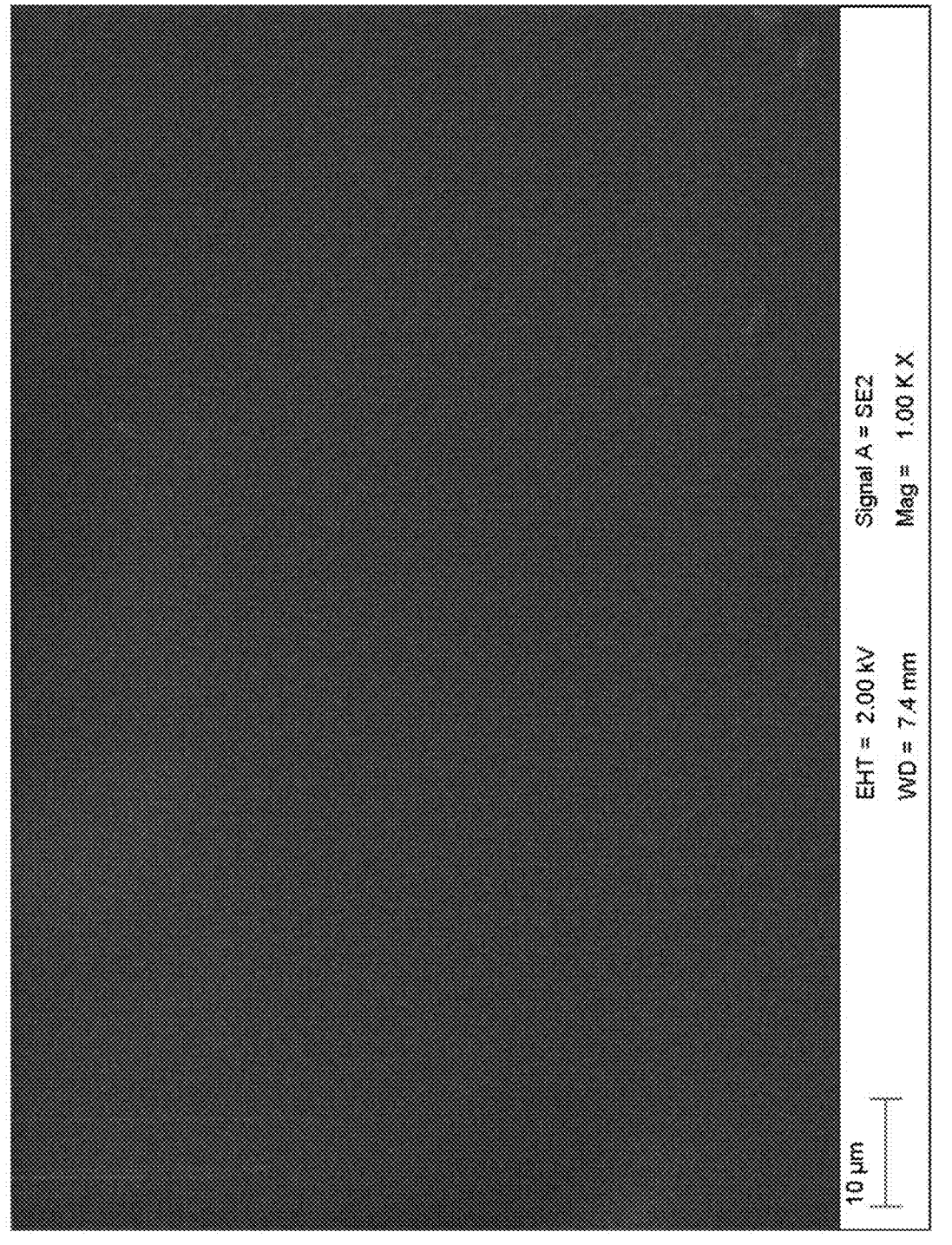
FIG. 10 is an SEM image of a poly(TA-Cu) coating prepared according to Example 2 of the disclosure.
Figure 11:
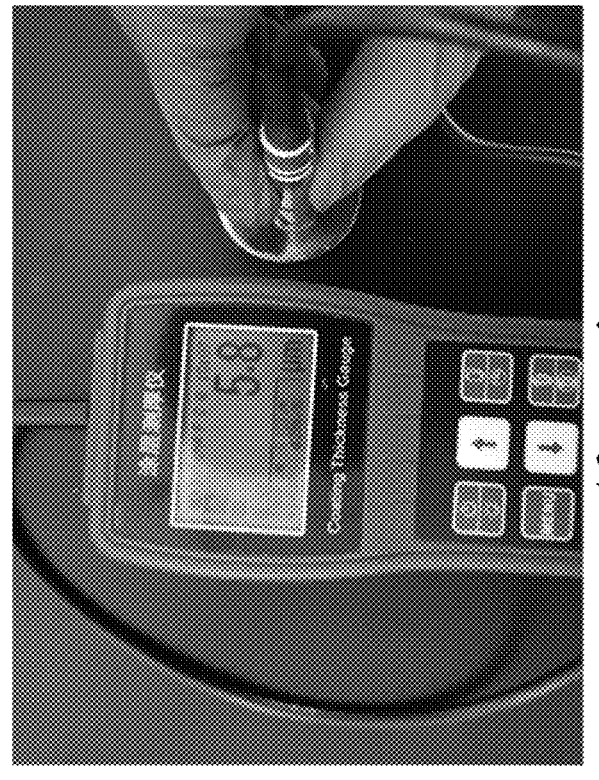
FIG. 11 shows a measurement of a thickness of a poly(TA-Cu) coating prepared according to Example 2 of the disclosure.
Figure 11:

An SEM examination was conducted on the poly(TA-Cu) coating formed on the surface of the 316L stainless steel material, as prepared in Example 2, and the results are shown in FIG. 10.
FIG. 10 shows an SEM image of the poly(TA-Cu) coating prepared in Example 2.
The SEM image confirms that the poly(TA-Cu) coating envelops the surface of the 316L stainless steel material, displaying uniform coverage.
FIG. 11 illustrates the measurement of a thickness of the poly(TA-Cu) coating prepared in Example 2. For accuracy, the identical procedure was employed to apply the poly(TA-Cu) coating onto a 316L stainless steel disc with a diameter of 40 mm and a thickness of 2 mm. As shown in FIG. 11, the poly(TA-Cu) coating has a thickness of 5.8 μm.
It will be obvious to those skilled in the art that changes and modifications may be made, and therefore, the aim in the appended claims is to cover all such changes and modifications.

What is claimed is:
1. A method for preparing a poly(thioctic acid)-copper coating (poly(TA-Cu)) on a surface of a cardiovascular stent material, comprising:
   grinding a cardiovascular stent material with sandpaper until a surface of the cardiovascular stent material is flat and smooth, rinsing the cardiovascular stent material with deionized water and anhydrous ethanol in sequence, and drying the cardiovascular stent material to obtain a pre-treated cardiovascular stent material;
   dissolving thioctic acid in an alcoholic solvent, adding anhydrous copper chloride to a mixed solution of thioctic acid and the alcoholic solvent, stirring the mixed solution, to yield a precursor solution; treating the pre-treated cardiovascular stent material with the precursor solution, and drying, thus forming a poly (thioctic acid)-copper coating on the surface of the pre-treated cardiovascular stent material;
wherein:
   a concentration of thioctic acid in the alcoholic solvent is 0.1-0.3 g/mL, and a molar ratio of anhydrous copper chloride to thioctic acid monomer is between 1:100 and 1:5000.
2. The method of claim 1, wherein the cardiovascular stent material is magnesium alloy, zinc alloy, iron alloy, 316L stainless steel, nickel titanium alloy, cobalt chromium alloy, or polylactic acid.
3. The method of claim 1, wherein the alcoholic solvent is anhydrous methanol or anhydrous ethanol.
4. The method of claim 1, wherein the cardiovascular stent material is treated with the precursor solution through dip coating, spin coating, or spray coating, to form the poly(thioctic acid)-copper coating on the surface of the pre-treated cardiovascular stent material.
5. The method of claim 1, further comprising disposing a magnesium fluoride conversion layer on the pre-treated cardiovascular stent material, which comprises submerging the pre-treated cardiovascular stent material into a hydrofluoric acid solution for 40-50 hours at 20-40° C., cleaning and drying a resulting product, to achieve the magnesium fluoride conversion layer on the pre-treated cardiovascular stent material; wherein the hydrofluoric acid solution has a concentration of 35-40 wt. %, and the poly(thioctic acid)-copper coating is formed on the magnesium fluoride conversion layer.

* * * * *